United States Patent [19]

Tajima et al.

[11] Patent Number: 4,888,371
[45] Date of Patent: Dec. 19, 1989

[54] BIS(2,6-DIS-TERT-BUTYL-4-BRANCHED PROPYL OR BUTYL PHENYL)-PENTAERYTHRITOL SPIRO PHOSPHITES AND SYNTHETIC RESIN COMPOSITIONS CONTAINING SUCH PHOSPHITES

[75] Inventors: Kenji Tajima, Kuwana; Tetsuo Tsuboi, Hatoyama; Ryozo Arata, Toin, all of Japan

[73] Assignee: Adeka Argus Chemical Co., Ltd., Urawa, Japan

[21] Appl. No.: 120,564

[22] Filed: Nov. 13, 1987

[30] Foreign Application Priority Data

May 14, 1986 [JP] Japan .................. 61-110099

[51] Int. Cl.$^4$ .................. C08K 5/52; C07F 9/15
[52] U.S. Cl. .................. 524/120; 558/78
[58] Field of Search .................. 558/78; 524/120

[56] References Cited

U.S. PATENT DOCUMENTS 4,415,686 11/1983 Chasar .................. 558/218
4,692,539 9/1987 Spivack .................. 558/78

FOREIGN PATENT DOCUMENTS 62-265351 11/1987 Japan .

Primary Examiner—Anton H. Sutto

[57] ABSTRACT

Bis(2,6-di tert butyl-4-branched propyl or butyl phenyl)-pentaerythritol spiro phosphites are provided having the formula:

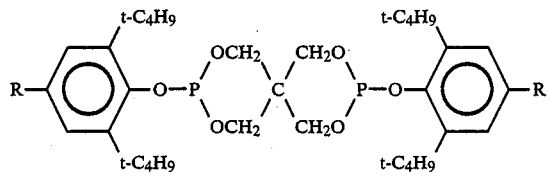

wherein R is a branched propyl or butyl group, such as isopropyl, iso-butyl, or sec-butyl, as well as synthetic resin compositions having enhanced resistance to deterioration upon exposure to the heat and light comprising such as bis(2,6-di-t-butyl-4-branched propyl or butyl phenyl)pentaerythritol spiro phosphites.

17 Claims, No Drawings

BIS(2,6-DIS-TERT-BUTYL-4-BRANCHED PROPYL OR BUTYL PHENYL)-PENTAERYTHRITOL SPIRO PHOSPHITES AND SYNTHETIC RESIN COMPOSITIONS CONTAINING SUCH PHOSPHITES

Synthetic resins such as polyethylene, polypropylene, polystyrene and polyvinyl chloride are subject to degradation upon exposure to heat and light, with resulting discoloration and deterioration of mechanical strength. Therefore, various stabilizers have been added to inhibit the deterioration of polymers, among them, phosphite compounds, which are important and effective stabilizers.

As a result of long extended research and development many special phosphites have been provided having improved stabilizing effectiveness and compatibility and ease of compounding with the resin and with other stabilizers.

L. Friedman, U.S. Pat. No. 3,047,608, patented July 31, 1962, discloses a class of spiro-bisphosphites having the formula:

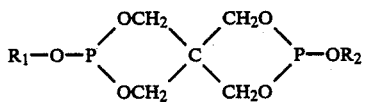

in which $R_1$ and $R_2$ are alkyl or aryl.

Hechenbleikner, U.S. Pat. No. 4,290,976, patented Sept. 22, 1981, states that dialkyl pentaerythritol diphosphites having the structural formula

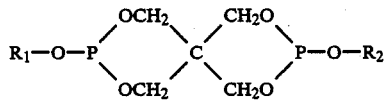

where $R_1$ and $R_2$ are alkyl groups, have been known for some time as effective stabilizers for vinyl polymers. They have been used primarily to stabilize vinyl chloride polymers and polyolefins, but have found use also in the stabilization of styrene polymers such as ABS.

U.S. Pat. No. 4,086,304, patented Apr. 25, 1978, to Hutton et al, provides organic triphosphites having improved hydrolytic stability and a process for stabilizing organic triphosphites.

The hydrolytically stable composition contains as its essential components at least about 85% by weight of an organic triphosphite and from about 0.1% to 5% by weight of a salt of a metal from Group I or Group II of the Periodic System and an organic acid having at least 8 carbon atoms.

Among the triphosphites disclosed are those having the formula:

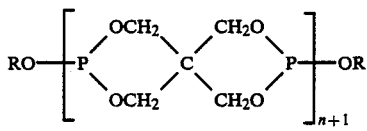

where n=0 or an integer from 1 to 8, and wherein the R's are the same or different and R is an aryl, alkyl, cycloalkyl, aralkyl or alkaryl group.

Typical examples of such phosphites include bis(-nonylphenyl) pentaerythrityl diphosphite, di-n-dodecyl pentaerythrityl diphosphite, and di-isodecyl pentaerythrityl diphosphite.

U.S. Pat. No. 4,180,498, patented Dec. 25, 1979, to Spivack provides compounds of the formula

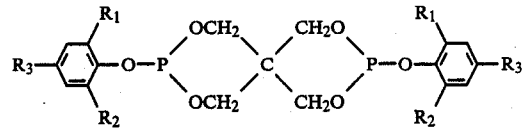

wherein:

$R_1$ and $R_2$ are independently lower alkyl or hydrogen, provided that only one of $R_1$ and $R_2$ is hydrogen;

$R_3$ is—$(A)_q$—COOR$_4$ or CN where

A is alkylene of 1 to 6 carbon atoms;

$R_4$ is alkyl of 1 to 24 carbon atoms, phenyl or alkyl substituted phenyl, and q is 0 or 1, which are suitable for stabilizing organic material against thermal, oxidative and ultraviolet light degradation.

U.S. Pat. No. 4,371,647, patented Feb. 1, 1983, to Minagawa et al, provides 2,6-di-tertiary butyl phenyl pentaerythritol spiro bisphosphites having the structure:

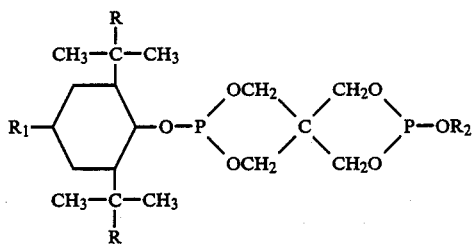

wherein:

R is alkyl having from one to six carbon atoms;

$R_1$ is methyl or ethyl;

$R_2$ is selected from the group consisting of alkyl having from one up to about eighteen carbon atoms; cycloalkyl having from three up to about twelve carbon atoms; and alkaryl and aryl having from six to about thirty carbon atoms; such groups substituted with from one to about four oxy ether —O— and/or carboxylic ester —COO— groups; the residue of a polyhydric alcohol having from two to about eighteen carbon atoms, and from two to about ten hydroxyl groups; and the residue of a polyphenol having from six to about eighteen carbon atoms and from two to about ten phenolic hydroxyl groups.

U.S. Pat. No. 4,385,145, patented May 24, 1983, to Horn, Jr., provides poly(alkylene terephthalate) compositions containing a stabilizing proportion of a pentaerythritol diphosphite ester.

The pentaerythritol diphosphite ester preferably is a bis-(alkylphenyl) or dialkyl pentaerythritol diphosphite. The alkylphenyl groups may include monoalkylphenyl, dialkylphenyl and trialkylphenyl groups although dialkylphenyl groups are preferred. Especially preferred are 2,4-dialkylphenyl groups. The alkyl groups should have 3–6 carbon atoms and tertiarybutyl groups are found most often because of their effect on solubility.

U.S. Pat. No. 4,496,677, patented Jan. 29, 1985, to Briggs, Jr. et al, provides a melt processable fluoropolymer composition stabilized against thermal degradation by incorporating therein a stabilizing system comprising (a) a hindered phenol pentaerythritol diphosphite, and (b) a salt of a carboxylic acid and a metal of Group II of the Periodic Table.

The hindered phenol pentaerythritol diphosphite has the general formula:

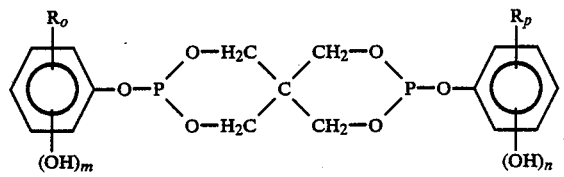

wherein the R substituents, which may be the same or different, are independently selected from the group consisting of hydrogen and alkyl, straight or branched chain, having from 1 to about 18 carbon atoms; and wherein m and n are integers from 0 to 2, and o and p are integers from 1 to 5, with the proviso that the sums of m+o, and n+p may not exceed 5. A preferred hindered phenol pentaerythritol is bis(2,4-di-t-butylphenyl)pentaerythritol diphosphite.

However, the bis spiro pentaerythritol diphosphites have not in general been characterized by good hydrolytic stability. In a moist environment they tend to undergo hydrolytic decomposition, with a corresponding loss of polymer-stabilizing effectiveness. Attempts to solve this problem of hydrolysis have utilized additives and these have been somewhat successful, but the problem remains, according to Hechenbleikner Hodan and Schall, U.S. Pat. No. 3,553,298, patented Jan. 5, 1971 suggested that the hydrolytic stability of phosphite esters of a wide class could be improved by combination therewith of an additive that is nitrogen-containing and selected from the group consisting of heterocyclic alkyl, nitrogen compounds, aromatic heterocyclic nitrogen compounds, dialkanolamines, trialkanolamines, ammonia and alkyl amines.

York, U.S. Pat. No. 4,116,926, patented Sept. 26, 1978 found triisopropanolamine to be a particularly effective stabilizer for dialkylpentaerythritol diphosphites and polyalkyl bisphenol-A polyphosphites.

The dialkylpentaerythritol diphosphites have the structural formula:

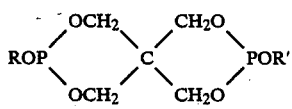

where R and R' are alkyl groups.

EPO Pat. No. 143,464, published June 5, 1985, to Argus Chemical Corporation, notes that most alkyl and alkylaryl pentaerythritol-spiro-bis phosphites having fourteen or more carbon atoms in the alkyl or alkylaryl groups, and indeed even pentaerythritol-spiro-bis phosphite itself, are solid materials. When their melting point is above 40° C., they are readily reduced to particulate form, and therefore are easily blended with other solid stabilizers for combination with synthetic resin. When however triisopropanolamine is used to improve hydrolytic stability, the desirable qualities of these pentaerythritol-spiro-bis-phosphites as an easily-handled particulate solid material are lost, and the material is converted into a sticky solid that is rather difficult to work with. It is not readily reduced to particulate form, and when in particulate form tends to agglomerate with itself and with other materials that are sought to be blended therewith, in formulating multicomponent stabilizer systems.

Argus accordingly employs long-chain aliphatic amines to improve the hydrolytic stability of pentaerythritol-spiro-bis-phosphites, and to form nonsticky solid compositions that are readily reduced to particulate form, and can easily be blended with other stabilizers and with synthetic resins, thus overcoming the stickiness problem inherent in the use of triisopropanolamine.

The pentaerythritol-spiro-bis-phosphite of these compositions have the formula:

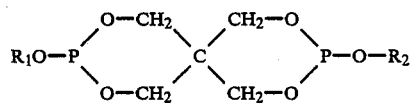

wherein: $R_1$ and $R_2$ are selected from the group consisting of alkyl and alkylaryl groups having at least fourteen carbon atoms up to about thirty-six carbon atoms.

$R_1$ and $R_2$ alkaryl groups in the phosphite include octylphenyl, 2,6-di-t-butyl-4-methylphenyl, 2,6-di-t-butyl-4-methoxycarbonyl, ethylphenyl, isooctylphenyl, t-octylphenyl, nonylphenyl, 2,4-di-t-butylphenyl, benzylphenyl and phenethylphenyl.

Exemplary pentaerythritol spiro-bis-phosphites include dimyristyl pentaerythritol diphosphite, dihexadecyl pentaerythritol diphosphite, distearyl pentaerythritol diphosphite, bis(2,4-di-t-butylphenyl) pentaerythritol diphosphite, di-(2,6-di-t-butylphenyl) pentaerythritol diphosphite, di-(2-t-butyl-4-methylphenyl) pentaerythritol diphosphite, 2,4-di-t-butyl-6-methylphenyl octylphenyl pentaerythritol diphosphite, 2,4-di-t-butyl-6-methylphenyl nonylphenyl pentaerythritol diphosphite, bis(2,6-di-t-butyl-4-methylphenyl) pentaerythritol diphosphite, bis(2,6-di-t-butyl-4-ethylphenyl) pentaerythritol diphosphite, 2,6-di-t-butyl-4-methylphenyl-2,6-di-t-butylphenyl pentaerythritol diphosphite, 2,6-di-t-butyl-4-methylphenyl-2,4-di-t-butylphenyl pentaerythritol diphosphite, 2,6-di-t-butyl-4-methylphenyl-2,4-di-t-octylphenyl pentaerythritol diphosphite, 2,6-di-t-amyl-4-methylphenyl phenyl pentaerythritol diphosphite, bis(2,6-di-t-amyl-4-methylphenyl) pentaerythritol diphosphite, bis(2,6-di-t-octyl-4-methylphenyl) pentaerythritol diphosphite.

However, the melting point of the alkylaryl phosphites, such as bis(2,4-di-t-butylphenyl) pentaerythritol diphosphite and bis(2,6-di-t-butyl-4-methylphenyl) pentaerythritol diphosphite, are above 235° C., and the compatibility thereof with many synthetic resins is not satisfactory. These problems are avoided, in the bis 2,6-di tert butyl phenyl pentaerythritol spiro phosphites by substituting a branched propyl or butyl group in the 40position of the phenyl group. These new pentaerythritol spiro bis phosphites have the formula:

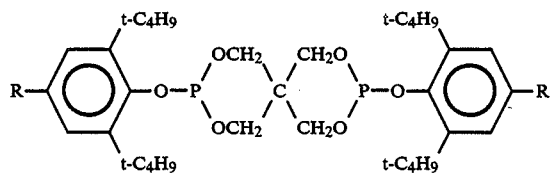

wherein R is isopropyl or iso or secondary butyl.

These pentaerythritol spiro bis phosphites have good hydrolytic stability. However, an aliphatic or cycloaliphatic or heterocyclic amine, as disclosed in Hodan et al, No. 3,553,298, York No. 4,116,926 or Argus EPO No. 143,464, the disclosures of which are hereby incorporated by reference, can be added to the spiro bisphosphite to improve the hydrolytic stability.

Exemplary amines include, for example, trialkanolamines such as triethanolamine, triisopropanolamine and tri-n-propanolamine; dialkanolamines such as diethanol dodecylamine, diethanol octadecylamine, diethanol oleylamine, diethanol octylamine, diethanol hexadecylamine, diisopropanol dodecylamine, diisopropanol octadecylamine and di-n-propanol octadecylamine; dialkanolamines such as diisopropanolamine and diethanolamine; alkanebis(dialkanolamines) such as ethylenebis(diethanolamine) and ethylenebis (diisopropanolamine); heterocyclic amines such as hexamethylenetetramine, piperidine, pyrrolidine, N-methyl piperidine, N-methylpyrrolidine, oxazolidine and isooxazolidine; and amine oxides such as lauryldimethyloxide and stearyldimethylamineoxide.

The preferred amount of the amine is from 0.01 to 5 parts by weight, preferably from 0.1 to 2 parts by weight, per 100 parts by weight of the spiro-bis phosphite.

Synthetic resins which can have their resistance to deterioration when exposed to heat and light enhanced by the spiro bisphosphites of this invention include α-olefin polymers and copolymers such as polyethylene, polypropylene, polybutene, poly-3-methylpentene, ethylene/vinylacetate copolymer and ethylene/propylene copolymer; halogen-containing resins such as polyvinyl chloride, polyvinyl bromide, polyvinyl fluoride, polyvinylidene chloride, chlorinated polyethylene, chlorinated polypropylene, chlorinated rubber, vinyl chloride/vinylacetate copolymer, vinyl chloride/ethylene copolymer, vinyl chloride/propylene copolymer, vinyl chloride/styrene copolymer, vinyl chloride/styrene/maleic anhydride terpolymer, vinyl chloride/butadiene copolymer, vinyl chloride/acrylic acid ester copolymer, vinyl chloride/methacrylic acid copolymer, vinyl chloride/acrylonitrile copolymer; polyvinyl acetate; polyacrylic acid and polyacrylic acid esters; polystyrene, copolymers of styrene with other copolymerizable monomers such as maleic anhydride, butadiene and acrylonitrile; acrylonitrile/butadiene/styrene terpolymer; acrylic acid ester/butadiene/styrene terpolymer; methacrylic acid ester/butadiene/styrene terpolymer; polymethyl methacrylate; polyvinyl alcohol; polyvinyl butyral; linear polyesters such as polyethylene terephthalate and polybutylene terephthalate; polyphenylene oxide; polyamide; polycarbonate; polyacetal; polyurethane; and epoxy resin.

The preferred amount of the spiro bisphosphite is within the range from about 0.01 to about 10 parts by weight per 100 parts by weight of the synthetic resin.

The spiro bisphosphites of this invention can be used together with other conventional heat and light stabilizers, such as, for example, phenolic antioxidants, thioether antioxidants, and ultraviolet light stabilizers.

Exemplary phenolic antioxidants which can be employed with the spiro bisphosphites include 2,6-di-t-butyl-p-cresol, 2,6-di-phenyl-4-octadecyloxyphenol, stearyl(3,5-di-t-butyl-4-hydroxyphenyl)-propionate, distearyl-3,5-di-t-butyl-4-hydroxybenzylphosphonate, thiodiethylenebis(3,5-di-t-butyl-4-hydroxyphenylpropionate, hexamethylenebis(3,5-di-t-butyl-4hydroxyphenyl- propionate, 4,4'-thiobis(6-t-butyl-m-cresol), 2-octylthio-4,6-bis(3,5-di-t-butyl-4-hydroxyphenoxy)-s-triazine, 2,2'-methylenebis(4-methyl-5-t-butylphenol), 2,2'-methylenebis(4-ethyl-6-t-butylphenol), bis(3,3-bis (4-hydroxy-3-t-butylphenyl)butylic acid) glycol ester, 4,4'-butylidenebis(6-t-butyl-m-cresol), 2,2'-ethylidenebis(4,6-di-t-butylphenol), 2,2'-ethylidenebis(4-sec-butyl-6-t-butylphenol), 3,6-dioxaoctylenebis(3-methyl-5-t-butyl-4-hydroxyphenylpropionate), 1,1,3-tris(2-methyl-4-hydroxy-5-t-butylphenyl) butane, bis(2-t-butyl-4-methyl-6-(2-hydroxy-3-t-butyl-5methyl benzyl)phenyl) terephthalate, 1,3,5-tris (2,6-dimethyl-3-hydroxy-4-t-butylbenzyl) isocyanurate, 1,3,5-tris(3,5-di-t-butyl-4-hydroxybenzyl) isocyanurate, 1,3,5-tris(3,5-di-t-butyl-4-hydroxybenzyl)-2,4,6-trimethylbenzene, 1,3,5-tris((3,5-di-t-butyl-4-hydroxyphenyl) propionyloxyethyl) isocyanurate, tetrakis (methylene-3-(3,5-di-t-butyl-4-hydroxyphenyl)-propionate) methane.

The thioether antioxidants which can be employed with the spiro bisphosphites of the invention include dialkylthiodipropionates such as dilauryl-, dimyristyl- and di-stearylthiodipropionate; and esters of β-alkylthiopropionic acid with polyhydric alcohols such as pentaerythritol tetrakis (β-dodecylthiopropionate).

The ultraviolet light stabilizers which can be employed with the spiro bisphosphites include hydroxybenzophenones such as 2-hydroxy-4-methoxybenzophenone, 2-hydroxy-4-n-octoxybenzephenone, 2,2'-dihydroxy-4-methoxybenzophenone and 2,4-dihydroxybenzophenone; benzotriazoles such as 2-(2'-hydroxy-3'-t-butyl-5'-methylphenyl)-5-chlorobenzotriazole, 2-(2'-hydroxy-3',5'-di-t-butylphenyl)-5-chlorobenzotriazole, 2-(2'-hydroxy-5'-methylphenyl) benzotriazole and 2-(2'-hydroxy-3',5'-di-t-amylphenyl) benzotriazole; benzoates such as phenyl salicylate, p-t-butylphenyl salicylate, 2,4-di-t-butylphenyl-3, 5-di-t-butyl-4-hydroxybenzoate and hexadecyl-3,5-di-t-butyl-4-hydroxybenzoate; Ni compounds such as 2, 2'-thiobis(4-t-octylphenol) Ni salt, (2,2'-thio bis(4-t-octylphenolate))-n-butylamine Ni and (3,5-di-t-butyl-4-hydroxybenzyl) phosphonic acid monoethyl ester Ni salt; substituted acrylonitriles such as α-cyano-β-methyl-β-(p-methoxyphenyl)acrylic) acid methyl ester; oxanilides such as N-2-ethylphenyl-N'-2-ethoxy-5-t-butylphenyloxanilide and N-2-ethylphenyl-N'-2-ethoxyphenyloxanilide; and piperidine compounds such as bis(2,2,6,6-tetramethyl-4-piperidyl) sebacate, bis(1,2,2,6,6-pentamethyl-4-piperidyl)-n-butyl-3,5-di-t-butyl-4-hydroxybenzylmalonate, bis(1-acryloyl-2,2,6,6-tetramethyl-4-piperidyl)-bis(3,5-di-t-butyl-4-hydroxybenzyl) malonate, tetrakis(2,2,6,6-tetramethyl-4-piperidyl)-butane, 1,2,3,4-tetracarboxylate, condensate of 1-(2-hydroxyethyl)-2,2,6,6-tetramethyl-4-piperidinol with diethylsuccinate and condensate of 2-t-octylamino-4,6-dichlorotriazine with 1,6-bis(2,2,6,6-tetramethyl-4-piperidylamino) hexane.

In addition, other conventional additives for synthetic resins, such as heavy metal deactivators, nucleating agents, metal soaps, plasticizers, flame retardants, lubricants, processing aids, blowing agents, pigments, fillers and antistatic agents can be employed.

The synthetic resins stabilized with the stabilizer of the invention can be in any physical form, including powders, filaments, yarns, films, sheets, molded articles, latex, foams and coatings.

The spiro bisphosphites can be readily prepared by reacting 2,6-di-t-butyl-4-R-phenol with pentaerythritol and phosphorous trichloride, in the presence of an acid acceptor. The following is an Example.

EXAMPLE I

Preparation of bis(2,6-di-t-butyl-4-sec-butyl-phenyl) spiro pentaerythritol diphosphite 2,6-Di-t-butyl-4-sec-butyl-phenol 57.8 g (0.220 mole), pentaerythritol 15.0 g (0.110 mole) and triethylamine 0.7 g were dissolved in 70 g of toluene. Phosphorous trichloride 31.5 g (0.229 mole) was added dropwise at room temperature over one hour under a stream of nitrogen.

The reaction mixture was stirred for 2 hours at 65° C., and then excess phosphorous trichloride was removed under vacuum. Triethylamine 24.4 g and tetraethyl ammonium bromide 0.7 g was added, and the reaction mixture was stirred for 5 hours at 80° C.

A white precipitate was produced by adding methanol to the solution. The white precipitate were filtered and recrystallized from n-hexane. The product, bis(2,6-di-t-butyl-4-sec-butyl-phenyl) spiro pentaerythritol diphosphite melted at 204.5°~205.5° C.

IR analysis: 1020 cm$^{-1}$ and 110 cm$^{-1}$ based on P—O—CH$_2$, 855 cm$^{-1}$ based on P—O—C (aromatic) and 1600 cm$^{-1}$ based on benzene ring.

The following Examples represent preferred embodiments of synthetic resin compositions of the invention.

EXAMPLES 1 to 3

Polypropylene compositions were prepared using spiro bisphophites of the invention and of the prior art, and having the following formulation:

| Ingredient | Parts by Weight |
| --- | --- |
| Polypropylene | 100 |
| Calcium stearate | 0.1 |
| Stearyl-(3,5-di-t-butyl-4-hydroxyphenyl)propionate | 0.1 |
| Spiro bisphosphite as shown in Table I | 0.1 |

The compositions were thoroughly blended in a mixer for 5 minutes, and then extruded to prepare pellets. (Cylinder temperature: 230° C. and 240° C., head die temperature: 250° C., velocity: 20 rpm). Test pieces were then molded by injection-molding at 250° C.

The test pieces were heated at 150° C. in a Geer oven, and the hours to failure were noted. The yellowness index of the pieces before and after exposure to fluorescent light for 72 hours was also noted.

the results are shown in Table I.

TABLE I

| Example No. | Spiro bisphosphite | Hours to Failure | Yellowness Index Original | Yellowness Index After 72 hours |
| --- | --- | --- | --- | --- |
| Control 1 | Bis(2,6-di-t-butyl-4-methyl-phenyl) pentaerythritol diphosphite | 240 | 9.2 | 13.1 |
| Control 2 | Bis(2,6-di-t-butyl-4-ethyl-phenyl) pentaerythritol diphosphite | 230 | 9.4 | 13.4 |
| Example 1 | Bis(2,6-di-t-butyl-4-sec-butyl-phenyl) pentaerythritol diphosphite | 280 | 8.7 | 11.1 |
| Example 2 | Bis(2,6-di-t-butyl-4-isopropyl-phenyl) pentaerythritol-diphosphite | 270 | 8.9 | 11.3 |
| Example 3 | Bis(2,6-di-t-butyl-4-isobutyl-phenyl) pentaerythritol-diphosphite | 270 | 9.0 | 11.3 |

TABLE I-continued

| Example No. | Spiro bisphosphite | Hours to Failure | Yellowness Index Original | Yellowness Index After 72 hours |
| --- | --- | --- | --- | --- |

It is apparent from the data that the spiro bisphosphites of the invention are superior to the prior art homologues of the controls.

EXAMPLES 4 to 6

Polypropylene compositions were prepared using spiro bisphosphites of the invention and of the prior art, and having the following formulation:

| Ingredient | Parts by Weight |
| --- | --- |
| Polypropylene | 100 |
| Calcium stearate | 0.2 |
| Pentaerythritol tetrakis((3,5-di-t-butyl-4-hydroxyphenyl) propionate) | 0.2 |
| Dilaurylthiodipropionate | 0.1 |
| Phosphite as shown in Table II | 0.1 |

The compositions were thoroughly blended in a mixer, and then extruded at 300° C. to prepare pellets. The extrusion was repeated for 5 times, to examine processing stability at high processing temperature. The melt index (MI:g/10 min) after the first and fifty extrusions was noted. The yellowness index of the pieces after immersion in NO$_x$ gas for 72 hours also was noted.

The results are shown in Table II.

TABLE II

| Example No. | Spiro bisphosphite | Yellowness Index | MI after extrusion for 1 time | MI after extrusion for 5 times | MI-5/MI-1 |
| --- | --- | --- | --- | --- | --- |
| Control | Bis(2,6-di-t-butyl-4-methyl-phenyl) pentaerythritol diphosphite | 12.8 | 2.8 | 6.5 | 2.32 |
| Example 4 | Bis(2,6-di-t-butyl-4-sec-butyl-phenyl) pentaerythritol diphosphite | 11.0 | 2.5 | 4.7 | 1.88 |
| Example 5 | Bis(2,6-di-t-butyl-4-isopropyl-phenyl) pentaerythritol diphosphite | 11.8 | 2.5 | 4.9 | 1.96 |
| Example 6 | Bis(2,6-di-t-butyl-4-isobutyl-phenyl) pentaerythritol diphosphite | 11.9 | 2.6 | 5.0 | 1.92 |

It is apparent from the data that the spiro bisphosphites of the invention are superior to the prior art homologue of the control.

EXAMPLES 7 to 9

Test pieces were prepared as in Example 1, and immersed in hot water at 70° C. for 12 days. The yellowness index of the pieces before and after immersion was noted. The results are shown in Table III.

TABLE III

| Example No. | Spiro bisphosphite | Yellowness Index Not immersed parts | Yellowness Index Immersed parts |
| --- | --- | --- | --- |
| Control 1 | Bis(2,6-di-t-butyl-4-methyl- | 7.8 | 8.5 |

TABLE III-continued

| Example No. | Spiro bisphosphite | Yellowness Index Not immersed parts | Immersed parts |
|---|---|---|---|
| | phenyl) pentaerythritol diphosphite | | |
| Control 2 | Bis(2,6-di-t-butyl-4-ethyl-phenyl) pentaerythritol diphosphite | 8.0 | 8.7 |
| Example 7 | Bis(2,6-di-t-butyl-4-sec-butyl-phenyl) pentaerythritol diphosphite | 7.3 | 7.8 |
| Example 8 | Bis(2,6-di-t-butyl-4-isopropyl-phenyl) pentaerythritol diphosphite | 7.5 | 8.1 |
| Example 9 | Bis(2,6-di-t-butyl-4-isobutyl-phenyl) pentaerythritol diphosphite | 7.6 | 8.1 |

It is apparent from the data that the spiro bisphosphites of the invention are superior to the prior art homologues of the controls.

EXAMPLES 10 to 12

High density polyethylene compositions were prepared using spiro bisphosphites of the invention and of the prior art, and having the following formulation.

| Ingredient | Parts by Weight |
|---|---|
| High density polyethylene | 100 |
| 3,9-Bis(1,1-dimethyl-2-($\beta$-(3-t-butyl-4-hydroxy-5-methylphenyl)propionyloxy)ethyl)-2,4,8,10-tetraoxaspiro(5.5) undecane | 0.05 |
| Phosphite shown in Table IV | 0.15 |

The stabilizers were blended with the polymer on a two-roll mill at 150° C. for 5 minutes, and sheets 1 mm thick were prepared by compression-molding of the blend at 150° C. and 180 kg/cm².

Test pieces 10×20 mm were cut off from the sheets, and heated in a Geer oven at 150° C. The hours to failure were noted, and the results are shown in Table IV.

TABLE IV

| Example No. | Spiro bisphosphite | Hours to Failure |
|---|---|---|
| Control | Bis(2,6-di-t-butyl-4-methylphenyl) pentaerythritol diphosphite | 480 |
| Example 10 | Bis(2,6-di-t-butyl-4-sec-butylphenyl) pentaerythritol diphosphite | 520 |
| Example 11 | Bis(2,6-di-t-butyl-4-isopropylphenyl) pentaerythritol diphosphite | 505 |
| Example 12 | Bis(2,6-di-t-butyl-4-isobutyl-phenyl) pentaerythritol diphosphite | 500 |

It is apparent from the data that the spiro bisphosphites of the invention are superior to the prior art homologue of the control.

EXAMPLES 13 to 15

Ethylene-vinyl acetate copolymer compositions were prepared using spiro bis phosphites of the invention and of the prior art, and having the following formulation:

| Ingredient | Parts by Weight |
|---|---|
| Ethylene-vinyl acetate copolymer | 100 |
| Montan wax lubricant | 0.2 |
| Triethylene glycol bis($\beta$-(3-t-butyl-4-hydroxy-5-methylphenyl) propionate) | 0.05 |
| Phosphite shown in Table V | 0.1 |

The stabilizers were blended with the polymer on a two-roll mill, and sheets 1 mm thick were prepared. Test pieces 2.5 cm square were cut off from the sheets, and heated in a Geer oven at 180° C.

The time when degradation set in and the initial color (Yellowness Index) of the sheets measured by a Hunter color differential meter were noted, and the results are shown in Table V.

TABLE V

| Example No. | Spiro bisphosphite | Onset of Heat Degradation | Yellowness Index |
|---|---|---|---|
| Control | Bis(2,6-di-t-butyl-4-methylphenyl) pentaerythritol diphosphite | 95 | 19 |
| Example 13 | Bis(2,6-di-t-butyl-4-sec-butylphenyl) pentaerythritol diphosphite | 110 | 16 |
| Example 14 | Bis(2,6-di-t-butyl-4-isopropylphenyl) pentaerythritol diphosphite | 105 | 17 |
| Example 15 | Bis(2,6-di-t-butyl-4-isobutyl-phenyl) pentaerythritol diphosphite | 105 | 17 |

It is apparent from the data that the spiro bisphosphites of the invention are superior to the prior art homologue of the control.

EXAMPLES 16 to 18

Polybutylene terephthalate compositions were prepared using spiro bisphosphites of the invention and of the prior art, and having the following formulation.

| Ingredient | Parts by Weight |
|---|---|
| Polybutylene terephthalate | 100 |
| Pentaerythritol tetrakis($\beta$-(3,5-di-t-butyl-4-hydroxyphenyl) propionate | 0.2 |
| Phosphite shown in Table VI | 0.2 |

The ingredients of the compositions were thoroughly blended in a mixer, and then injection-molded to prepare test specimens.

The specimens were heated at 150° C. for 300 hours, and tensile strength before and after heating was noted. The % tensile strength retained is shown in Table VI.

TABLE VI

| Example No. | Spiro bisphosphite | % Tensile Strength Retained |
|---|---|---|
| Control 1 | None | 65 |
| Control 2 | Bis(2,6-di-t-butyl-4-methylphenyl) pentaerythritol diphosphite | 71 |
| Example 16 | Bis(2,6-di-t-butyl-4-sec-butylphenyl) pentaerythritol diphosphite | 78 |
| Example 17 | Bis(2,6-di-t-butyl-4-isopropylphenyl) pentaerythritol diphosphite | 75 |
| Example 18 | Bis(2,6-di-t-butyl-4-isobutylphenyl) pentaerythritol | 76 |

TABLE VI-continued

| Example No. | Spiro bisphosphite | % Tensile Strength Retained |
|---|---|---|
| | diphosphite | |

It is apparent from the data that the spiro bisphosphites of the invention are superior to the prior art homologues of the controls.

EXAMPLES 19 to 21

Polyphenylene oxide resin compositions were prepared using spiro bisphosphites of the invention and of the prior art, and having the following formulation:

| Ingredient | Parts by Weight |
|---|---|
| Poly(2,6-dimethyl-1,4-phenyleneoxide | 50 |
| Polystyrene | 47.5 |
| Polycarbonate | 2.5 |
| TiO$_2$ | 3.0 |
| 1,1,3-Tris(2-methyl-4-hydroxy-5-t-butylphenyl) butane | 0.1 |
| Phosphite shown in Table VII | 0.1 |

The ingredients of the compositions were mixed and then extruded, followed by injection-molding to prepare test pieces. The heat stability was evaluated by heating the test pieces in a Geer oven at 125° C. for 100 hours. Elongation and Izod impact strength were measured before and after the heating, and the percent elongation and percent Izod impact strength retained were calculated.

The results are shown in Table VII.

TABLE VII

| Example No. | Spiro bisphosphite | % Elongation Retained | % Impact Strength Retained |
|---|---|---|---|
| Control 1 | Bis(2,6-di-t-butyl-4-methylphenyl) pentaerythritol diphosphite | 65 | 74 |
| Control 2 | Bis(2,6-di-t-butyl-4-ethylphenyl) pentaerythritol diphosphite | 63 | 71 |
| Example 19 | Bis(2,6-di-t-butyl-4-sec-butylphenyl) pentaerythritol diphosphite | 67 | 79 |
| Example 20 | Bis(2,6-di-t-butyl-4-isopropylphenyl) pentaerythritol diphosphite | 66 | 76 |
| Example 21 | Bis(2,6-di-t-butyl-4-isobutylphenyl) pentaerythritol diphosphite | 66 | 76 |

It is apparent from the data that the spiro bisphosphites of the invention are superior to the prior art homologues of the controls.

EXAMPLES 22 to 24

Cis-1,4-isoprene polymer (M.W. 680,000) 100 g and 0.5 g of the spiro bisphosphite shown in Table VIII were dissolved in 250 ml of isooctane, and then the isooctane was evaporated.

The polyisoprene compositions were heated in a Geer oven at 100° C. for 4 hours, and the color of the compositions was observed. The inherent viscosity (in toluene) was measured before and after heating.

The results are shown in Table VIII.

TABLE VIII

| Example No. | Spiro bisphosphite | Color after Heating | Inherent Viscosity ($\eta$) Original | Inherent Viscosity ($\eta$) After Heating |
|---|---|---|---|---|
| Control | Bis(2,6-di-t-butyl-4-methylphenyl) pentaerythritol diphosphite | Yellow | 4.2 | 3.6 |
| Example 22 | Bis(2,6-di-t-butyl-4-sec-butylphenyl) pentaerythritol diphoshite | Pale Yellow | 4.5 | 4.0 |
| Example 23 | Bis(2,6-di-t-butyl-4-isopropylphenyl) pentaerythritol diphosphite | Pale Yellow | 4.4 | 3.9 |
| Example 24 | Bis(2,,6-di-t-butyl-4-isobutylphenyl) pentaerythritol diphosphite | Pale Yellow | 4.4 | 3.9 |

It is apparent from the data that the spiro bisphosphites of the invention are superior to the prior art homologue of the control.

EXAMPLES 25 to 27

Polycarbonate resin compositions were prepared having the following formulation:

| Ingredient | Parts by Weight |
|---|---|
| Polycarbonate | 100 |
| Spiro bisphosphite shown in Table IX | 0.15 | the ingredients were mixed and compression-molded at 260° C. to prepare sheets 1 mm thick. Heat stability was evaluated by heating the sheets in a Geer oven at 230° C. for 45 minutes, and then observing the color of sheets.

The results are shown in Table IX.

TABLE IX

| Example No. | Spiro bisphosphite | Color of Sheets |
|---|---|---|
| Control 1 | None | Yellowish Brown |
| Control 2 | Bis(2,6-di-t-butyl-4-methylphenyl) pentaerythritol diphosphite | Yellow |
| Example 25 | Bis(2,6-di-t-butyl-4-sec-butylphenyl) pentaerythritol diphosphite | Pale Yellow |
| Example 26 | Bis(2,6-di-t-butyl-4-isopropylphenyl) pentaerythritol diphosphite | Pale Yellow |
| Example 27 | Bis(2,6-di-t-butyl-4-isobutylphenyl) pentaerythritol diphosphite | Pale Yellow |

It is apparent from the data that the spiro bisphosphites of the invention are superior to the prior art homologues of the controls.

EXAMPLES 28 to 30

Acrylonitrile-butadiene-styrene terpolymer resin compositions were prepared using spiro bisphosphites of the invention and of the prior art, and having the following formulation:

| Ingredient | Parts by Weight |
|---|---|
| Acrylonitrile-butadiene-styrene terpolymer | 100 |
| Calcium stearate | 1.0 |

-continued

| Ingredient | Parts by Weight |
|---|---|
| Tris(3,5-di-t-butyl-4-hydroxybenzyl) isocyanurate | 0.2 |
| Phosphite shown in Table X | 0.1 |

The ingredients were thoroughly mixed and the compositions then extruded at 200° C. to prepare pellets. Test pieces were then molded by injection molding at 230° C.

The test pieces were heated at 135° C. in a Geer oven for 30 hours. The whiteness index of the pieces after heating was determined by a Hunter color difference meter. The Izod impact strength (kg.cm/cm) before and after heating was also measured.

The results are shown in Table X

| Example No. | Spiro bisphosphite | Whiteness Index | Izod impact strength Original | Izod impact strength After Heating |
|---|---|---|---|---|
| Control 1 | Bis(2,6-di-t-butyl-4-methylphenyl) pentaerythritol diphosphite | 36.2 | 18.1 | 16.5 |
| Control 2 | Bis(2,6-di-t-butyl-4-ethylphenyl) pentaerythritol diphosphite | 34.8 | 17.8 | 15.9 |
| Example 28 | Bis(2,6-di-t-butyl-4-sec-butylphenyl) pentaerythritol diphosphite | 38.7 | 18.7 | 17.5 |
| Example 29 | Bis(2,6-di-t-butyl-4-isopropylphenyl) pentaerythritol diphosphite | 37.5 | 18.5 | 17.2 |
| Example 30 | Bis(2,6-di-t-butyl-4-isobutylphenyl) pentaerythritol diphosphite | 37.4 | 18.5 | 17.2 |

It is apparent from the data that the spiro bisphosphites of the invention are superior to the prior art homologues of the controls.

Having regard to the foregoing disclosure the following is claimed as the inventive and patentable embodiments thereof:

1. Bis(2,6-di-tert-butyl-4-branched propyl or butyl phenyl)-pentaerythritol spiro phosphites having the formula:

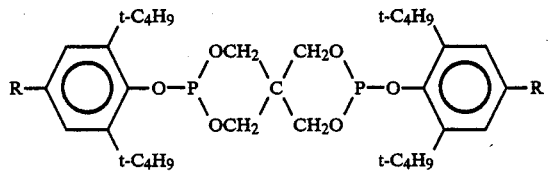

wherein both R's are selected from the group consisting of isopropyl, iso-butyl, and sec-butyl.

2. Bis(2,6-di-tert-butyl-4-branched propyl or butyl phenyl)-pentaerythritol spiro phosphites according to claim 1 wherein R is isopropyl.

3. Bis(2,6-di-tert-butyl-4-branched propyl or butyl phenyl)-pentaerythritol spiro phosphites according to claim 1 where R is isobutyl.

4. Bis(2,6-di-tert-butyl-4-branched propyl or butyl phenyl)-pentaerythritol spiro phosphites according to claim 1 wherein R is sec-butyl.

5. A polyvinyl chloride resin composition having improved resistance to deterioration upon exposure to heat and light comprising a polyvinyl chloride resin formed at least in part of the recurring group:

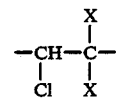

and having a chlorine content in excess of 40%, where X is either hydrogen or chlorine; and a phosphite in accordance with claim 1.

6. A polyvinyl chloride resin composition in accordance with claim 5 in which the polyvinyl chloride resin is polyvinyl chloride homopolymer.

7. A polyvinyl chloride resin composition in accordance with claim 5 in which the polyvinyl chloride resin is a copolymer of vinyl chloride and vinyl acetate.

8. An olefin polymer composition having improved resistance to deterioration upon exposure to heat and light comprising an olefin polymer selected from the group consisting of polymers of alpha-olefins having from two to six carbon atoms and polystyrene, and a phosphite in accordance with claim 1.

9. An olefin polymer composition in accordance with claim 8 wherein the polyolefin is polypropylene.

10. An olefin polymer composition in accordance with claim 8 wherein the polyolefin is polyethylene.

11. An olefin polymer composition in accordance with claim 8 wherein the polyolefin is ethylene-propylene copolymer.

12. An olefin polymer composition in accordance with claim 8 wherein the polyolefin is cis-1,4-isoprene polymer.

13. An ethylene-vinyl acetate copolymer composition having improved resistance to deterioration upon exposure to heat and light comprising an ethylene-vinyl acetate copolymer and phosphite in accordance with claim 1.

14. An acrylonitrile-butadiene-styrene copolymer composition having improved resistance to deterioration upon exposure to heat and light comprising an acrylonitrile-butadiene-styrene copolymer and a phosphite in accordance with claim 1.

15. A polyester resin composition having improved resistance to deterioration upon exposure to heat and light comprising a polyester and a phosphite in accordance with claim 1.

16. A polyester resin composition according to claim 15 in which the polyester is polybutylene terephthalate.

17. A polycarbonate resin composition having improved resistance to deterioration upon exposure to heat and light comprising a poly carbonate and a phosphite in accordance with claim 1.

* * * * *